United States Patent [19]

Kieczykowski et al.

[11] Patent Number: 4,922,007

[45] Date of Patent: May 1, 1990

[54] PROCESS FOR PREPARING 4-AMINO-1-HYDROXYBUTYLIDENE-1,1-BISPHOSPHONIC ACID OR SALTS THEREOF

[75] Inventors: Gerard R. Kieczykowski, Westfield; David G. Melillo, Scotch Plains; Ronald B. Jobson, East Brunswick, all of N.J.

[73] Assignee: Merck & Co., Inc., Rahway, N.J.

[21] Appl. No.: 363,820

[22] Filed: Jun. 9, 1989

[51] Int. Cl.$^5$ ............................................. C07F 9/38
[52] U.S. Cl. ............................................. 562/13
[58] Field of Search ................................ 562/13

[56] References Cited

U.S. PATENT DOCUMENTS

| | | |
|---|---|---|
| 4,054,598 | 10/1977 | Blum et al. . |
| 4,267,108 | 5/1981 | Blum et al. . |
| 4,304,734 | 12/1981 | Jary et al. . |
| 4,327,039 | 4/1982 | Blum et al. . |
| 4,407,761 | 10/1983 | Blum et al. .................... 562/13 |
| 4,621,077 | 11/1986 | Rosini . |
| 4,639,338 | 1/1987 | Stahl et al. .................... 562/13 |

*Primary Examiner*—J. E. Evans
*Attorney, Agent, or Firm*—Charles M. Caruso; Hesna J. Pfeiffer

[57] ABSTRACT

A process for the preparation of 4-amino-1-hydroxybutylidene-1, 1-bisphosphonic acid or salts thereof which comprises:
(a) reacting 4-aminobutyric acid with a mixture of phosphorous acid and PCl$_3$ in the presence of methanesulfonic acid; and
(b) recovering said 4-amino-1-hydroxybutylidene-1, 1-bisphosphonic acid or salts thereof.

5 Claims, No Drawings

PROCESS FOR PREPARING 4-AMINO-1-HYDROXYBUTYLIDENE-1,1-BIS-PHOSPHONIC ACID OR SALTS THEREOF

BACKGROUND OF THE INVENTION

This invention relates to an improved process for making 4-amino-1-hydroxybutylidene-1,1-bisphosphonic acid or salts thereof, where the end product is obtained in particularly pure form and at high yields in a one-pot procedure.

It is known according to U.S. Pat. No. 4,407,761 to prepare 4-amino-1-hydroxybutylidene-1,1-bisphosphonic acid by reacting an aminocarboxylic acid with a phosphonating reactant and then hydrolyzing the reaction mixture by addition of concentrated hydrochloric acid with heating. Problems result from this reaction whereby it does not remain homogeneous and local solidification occurs. This solidificaiton causes variable yields, which in part results from the exothermic nature of the reaction with development of hot spots. Morever, to make the sodium salt utilizing the prior art processes required isolation of 4-amino-1-hydroxybutylidine-1,1-bisphonic acid and an additional step to convert to the monosodium salt.

The present invention solves there problems by allowing the reaction to remain fluid and homogeneous making commerical manufacturing possible, reducing the number of process steps and providing a large improvement in isolated yield of from about 45–50% to about 85–90%.

SUMMARY OF THE INVENTION

The present invention provides a process for the preparation of 4-amino-1-hydroxybutylidene-1,1-bisphosphonic acid or salts thereof which comprises:
(a) reacting 4-aminobutyric acid with a mixture of phosphorous acid and $PCl_3$ in the presence of methanesulfonic acid; and
(b) recovering said 4-amino-1-hydroxybutylidene-1,1-bisphosphonic acid or salts thereof.

The reaction can be conducted, if desired, in the presence of an inert organic diluent which does not solubilize the reaction product and at a temperature of from about 45° C. to 125° C., although this is not necessary when methanesulfonic acid is used.

DETAILED DESCRIPTION OF THE INVENTION

It has been found that pure crystallize 4-amino-1-hydroxybutylidene-1,1-bisphosphonic acid or salts thereof can surprisingly be obtained in high yields when using the procedure of the invention. The invention involves the reaction of an aminoalkane carboxylic acid with phosphonating reactants in the presence of methanesulfonic acid and recovering 4-amino-1-hyroxyutylidene-1,1-bisphosphonic acid or salts thereof. The compound is crystallized directly from the reaction mixture in about 90% yield after quenching, hydrolysis, and pH adjustment to about 4.3 with no further purification necessary.

The aminoalkane carboxylic acids which can be used is 4-aminobutyric acid. The phosphonylation reaction generally takes place at temperatures of from 45° to 125° C., preferably at about 65° C.

Preferably 1 to 2, particularly 1.5 moles of $H_3PO_3$ and 1 to 2.5, particularly 2.4 mols of $PCl_3$ are used per mol of aminocarboxylic acid. If desired, inert organic diluents, which do not solublize the reaction product, particularly hexane or chlorinated hydrocarbons, such as chlorobenzene, tetrachloroethane, tetrachloroethylene and trichloroethylene can be used in the reaction. It is not necessary to use a diluent when methanesulfonic acid is used in the reaction.

In general, the hydrolysis is completed after about 3 hours boiling under reflux, as is shown by the chromatographic test of the reactin solution.

The reaction is schematically represented as follows:

$H_2NCH_2CH_2CH_2CO_2H$ 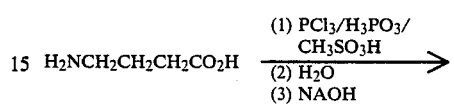

$C_4H_9NO_2$
MW 103.12

 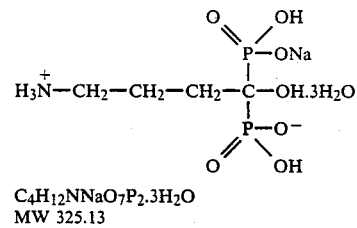

$C_4H_{12}NNaO_7P_2.3H_2O$
MW 325.13

4-amino-1-hydroxybutylidene-1,1-bisphosphonic acid monosodium salt trihydrate described here is useful as a pharmaceutical composition and for the treatment or prevention of diseases involving bone resorption. Such diseases as hypercalcemia of malignancy, Paget's disease, and osteoporosis are advantageously treated with 4-amino-1-hydroxybutylidene-1,1-bisphosphonic acid monosodium salt trihydrate made according to the process of the present invention.

Other pharmaceutically acceptable salts, such as for example the calcium, potassium salts, can be prepared according to the processes of the present invention and are included within the scope thereof.

The following examples are illustrative of the practice of the invention without being limiting in any way.

EXAMPLE 1

Preparation of 4-amino-1-hydroxybutylidene-1,1-bisphosphonic acid monosodium salt trihydrate A 250 mL flask was fitted with a mechanical stirrer, a thermcouple, an addition funnel and a reflux condenser through which is circulated −20° C. brine. The system was connected to a caustic scrubber which places a back pressure of 7–10 psi on the system. The system was flushed with nitrogen and charged with 20 g (0.19 mol) of aminobutyric acid, 80 mL of methanesulfonic acid, and 24 g (0.29 mol) of phosphorous acid. For larger scale operations, the methanesulfonic acid can be charged first, followed by the 4-aminobutyric acid and phosphorus acid. Upon mixing, the heat of neutralization and solution increased the reaction temperature to 75° C. The suspension was aged for 15 minutes at 70°–75° C. resulting in clear colorless solution. The solution was cooled to 35° C. and phosphorus trichloride ($PCl_3$), 40 mL (0.46 mol) was added cautiously over 20 minutes. The reaction was then heated to 65° C. and aged at that temperature for 20 hours. The reaction should not be allowed to get much above 65° C. The reaction becomes self-heating above 85° C. and under adiabatic conditions the temperature will increase steadily. At about 150 degrees an exotherm accompanied by a large pressure release occurs. It is therefore recommended that the reaction be immediately quenched into cold water if the temperature reaches 85° C. The reaction was then cooled to 25° C. and added to 200 mL of deionized water over 5 minutes. The flask was rinsed with an additional 100 mL of water and the combined solution aged at 95°–100° C. for 5 hours. The reaction was cooled to 20° C. and maintained at 20°–25° C. while the pH was adjusted to 4.3 with ca. 80 mL of 50% NaOH. The resulting white suspension was then cooled to 0°–5° C. and aged for 1 hour. The pH was readjusted to 4.3 if necessary and the suspension aged at 0°–5° C. for an additional 2 hours. The product was collected by filtration, then washed with 2×50 mL of cold (0°–5° C.) water and 100 mL of 95% EtOH. The yield after air drying at 40° C. to constant weight was 56.4 g (90%).

EXAMPLE 2

Analysis of 4-amino-1-hydroxybutylidene-1,1-bisphosphonic acid monosodium salt trihydrate The reaction product of Example 1 was analysed with the results as follows:

| Tests | Results |
| --- | --- |
| color,form,appearance | fine white free flowing crystalline powder |
| Particle size | 10–100μ, average <50 |
| Melting point | inserted at 245, starts to melt at 257, decomposes at 262.5 |
| Assay (NaOH titration) | 99.7% |
| Assay (complexometric tritration) | 99.9% |
| HPLC | 99.5% |
| Karl Fisher | 16.6% (theory 16.6%) |
| Loss on drying | 16.7% |
| GC-residual ethanol | <0.01% |
| TLC for other acids | <0.01% (not detected) |
| Heavy metals | <20 ppm |
| pH of 0.5% H$_2$O solution | 4.36 |
| IR | conforms |
| X-ray | conforms |
| Flame test for Na | conforms |
| Microchemical analysis | |

| | Theory | Found |
| --- | --- | --- |
| Carbon | 14.77 | 14.67 |
| Hydrogen | 5.54 | 5.58 |
| Nitrogen | 4.31 | 4.22 |
| Sodium* | 7.08 | 7.00 |
| Phosphorous | 19.08 | 19.00 |
| Residual chloride | | <0.05 |

*Determined by AA.

EXAMPLE 3

Preparation of 4-amino-1-hydroxybutylidene-1,1-bisphosphonic acid

To isolate the bisphosphonic acid, the pH was adjusted to 1.8 rather than 4.32 as follows: The reaction was cooled to 20 degrees C. and maintained at 20–25 degrees C. while the pH was adjusted to 1.0 with about 80 mL of 50% NaOH. The resulting white suspension was then cooled to 0–5 degrees C. and aged for 1 hour. The pH was adjusted to 1.8 and the suspension aged at 0–5 degrees C. for an additional 2 hours. The product was collected by filtration and washed with 100 mL of 20 degrees C. deionized water, then air dried at 40 degrees C. yielding 44.0 g (86% yield) of white crystalline product.

EXAMPLE 4

Analysis of 4-amino-1-hydroxybutylidene-1,1-bisphosphonic acid

The reaction product of Example 3 was analysed with the results as follows:

| Tests | Results |
| --- | --- |
| Color,form,appearance | Clean, crystalline, white powder |
| NaOH titration | 99.5% |
| Complexometric titration | 99.8% |
| Loss on drying | 6.79% (theory 6.74) |
| pH of 0.5% solution | 2.15% |
| Miccrochemical analysis C$_4$H$_{13}$NO$_7$P$_2$·H$_2$O | |

| | Theory | Found |
| --- | --- | --- |
| Carbon | 17.97 | 17.84 |
| Hydrogen | 5.62 | 5.55 |
| Nitrogen | 5.24 | 5.16 |
| Sodium* | — | .05* |
| Phosphorous | 23.21 | 23.02 |

*By atomic absorbtion spectroscopy. The other elements are determined by combustion analysis.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A process for the preparation of 4-amino-1-hydroxybutylidene-1,1-bisphosphonic acid or salts thereof which comprises:
    (a) reacting 4-aminobutyric acid with a mixture of phosphorous acid and PCl$_3$ in the presence of methanesulfonic acid; and
    (b) recovering said 4-amino-1-hydroxybutylidene-1,1-bisphosphonic acid or salts thereof.

2. The process of claim 1 wherein said reaction is conducted at a temperature of from 45° C. to 125° C.

3. The process of claim 2 wherein said reaction is conducted at a temperature of about 65° C.

4. The process of claim 3 wherein sufficient sodium hydroxide is added to the reaction mixture and 4-amino-1-hydroxybutylidene-1,1-bisphosphonic acid monosodium salt trihydrate is recovered.

5. The process of claim 3 wherein 4-amino-1-hydroxybutylidene-1,1-bisphosphonic acid is recovered.

* * * * *